United States Patent [19]

Buehler

[11] 4,127,650

[45] Nov. 28, 1978

[54] MEDICINAL SIMETHICONE CONTAINING COMPOSITION AND ITS METHOD OF PRODUCTION

[75] Inventor: John D. Buehler, Fort Washington, Pa.

[73] Assignee: William H. Rorer, Inc., Fort Washington, Pa.

[21] Appl. No.: 563,917

[22] Filed: Mar. 31, 1975

[51] Int. Cl.² ............... A61K 9/30; A61K 31/695; A61K 33/00; A61K 33/10
[52] U.S. Cl. .................................. 424/184; 424/31; 424/127; 424/128; 424/131; 424/154; 424/155; 424/156; 424/157; 424/177
[58] Field of Search .............. 424/184, 157, 31, 35, 424/127, 128, 131, 154, 155, 156, 177

[56] References Cited

U.S. PATENT DOCUMENTS

| | | | |
|---|---|---|---|
| 2,922,747 | 1/1960 | Scanlan | 424/35 |
| 2,926,121 | 2/1960 | Hobbs et al. | 424/35 |
| 3,538,214 | 11/1970 | Polli et al. | 424/19 |
| 3,767,794 | 10/1973 | McVean et al. | 424/184 |

FOREIGN PATENT DOCUMENTS 1,129,260  10/1968  United Kingdom ............ 424/184

*Primary Examiner*—Frederick E. Waddell
*Attorney, Agent, or Firm*—James A. Nicholson; Raymond Underwood

[57] ABSTRACT

Simethicone is entrapped in solid, discrete particles of a matrix composition of glycerol and corn syrup solids. A mixture of these particles and a therapeutic antacid overcomes the incompatability of the simethicone and the antacid, due to the shielding action of the matrix composition.

14 Claims, No Drawings

MEDICINAL SIMETHICONE CONTAINING COMPOSITION AND ITS METHOD OF PRODUCTION

This invention relates to pharmaceutical formulations for the relief of flatulence and more particularly to orally consumable compositions which contain an agent having gas reducing properties. The invention also concerns the process for producing the formulations.

Flatulence is a form of dyspepsia which is caused by an excessive accumulation of gas in the stomach or intestines. It may be air which has been carried down in the stomach along with food or liquid which was consumed. Or the gas may be formed by the fermentation or putrefaction of ingested foods. If the gas cannot be expelled by eructation or the passage of flatus, the accumulated gas produces a sensation of pressure or fullness in the epigastrium or the precordial region. In some cases the abdominal distension may be so severe that an oppressive, suffocating sensation is experienced. Even in moderate cases, the sufferer is anxious to obtain relief from the flatulence as soon as possible.

An agent which is commonly administered orally to manage the excess gas of flatulence is simethicone, to take advantage of its defoaming action. This silicon containing compound has the property of reducing large amounts of gas and as this occurs quite promptly the patient's distended and bloated feeling is promptly overcome. Generally, from 20 to 40 milligrams of simethicone is administered as a unit dose.

As flatulence is frequently accompanied with gastric hyperacidity, it is a common practice to administer an antacid along with the simethicone. For ease of consumption, the antacid and simethicone are combined in a single compressed tablet. The antacid component may be one or more of the usual pharmaceutical alkaline compounds administered for this purpose.

The combination of the simethicone and antacid in a single tablet or capsule has the advantage of assuring that they are in a proper relative ratio and are jointly consumed but tests have shown that the simethicone's gas reducing properties are impaired by the antacid. To overcome this incompatability, either the simethicone or the antacid has been coated with or entrapped within a protective material. Usually, the microscopic droplets of simethicone are initially enclosed in the insulating material, the antacid (or antacids) is mixed therewith and the mixture is tableted or encapsulated, or a separate layer is prepared.

In accordance with the present invention, the droplets of simethicone are enclosed in a coating composition which is a mixture of glycerol and corn syrup solids. The glycerol and corn syrup solids are both inexpensive and are easily digested and consequently they constitute an ideal coating composition. In contrast, the materials which have been employed in the past, such as sorbitol, are more expensive.

Generally considered, to practice the process of the invention, the glycerol and corn syrup solids are combined and heated to a molten state during mixing or agitation and to this molten syrup is then added the liquid simethicone while the blending is continued. This forms an emulsion in which the glycerol-corn syrup solids mixture is the external continuous phase and the micro droplets of simethicone are the internal phase.

The emulsion of simethicone and the glycerol-corn syrup solids mixture is then cooled or is allowed to cool to room temperature or below so that it is fragile and brittle. It is then broken, crushed, ground or otherwise comminuted to particles of a small size. The particles should preferably be between a 12 and 14 mesh (U.S.S.S.) size as this will best assure that most of the simethicone is not exposed or released. The entrapment of the simethicone in the glycerol-corn syrup matrix serves to protect the simethicone against inactivation in the presence of an antacid. As some simethicone may have been released in the comminuting process, it is best to wash the particles in a solvent which will remove the free simethicone, as will be explained.

These particles of simethicone in the solid matrix can be consumed or sold or stored in this form or tablets can be compressed from them; their palpable taste will appeal to the consumer. Or, as is mentioned above, the particles of the simethicone and enclosing matrix may advantageously be combined with one or more antacids to produce a composition or tablet. This combination product has the dual therapeutic action of relieving flatulence and hyperacidity. Moreover, the simethicone will remain stable as it is insulated from the antacid.

Considering the invention more specifically, the glycerol is preferably of a pharmaceutical grade and as it is a liquid it readily dissolves the corn syrup solids especially when heated. The corn syrup solids which are preferably used are commercially available as a granular product of 42 D.E. (dextrose equivalent) and contain not less than 3% moisture. However, corn syrup or corn syrup-corn syrup solids mixtures, or solutions having higher initial moisture contents may be used.

The glycerol should amount to from about 2% to about 15%, preferably 4% to 9%, of the total weight of the syrup mixture with the corn syrup solids. This syrup mixture is heated to a temperature between about 110° and 130° C., during continuous agitation, mixing or stirring so that a uniform, homogeneous syrup is produced. While this blending is continued, the simethicone is added and the agitation is continued until it is assured that a thorough dispersion has been achieved. The temperature of the syrup may be allowed to drop to about 90° C. during this latter agitation as the syrup will not get too viscous.

The simethicone content of its mixture with the syrup may be as high as 20% w/w but somewhat more simethicone may be added if it is found that it does not impair the hardening and brittleness of the particular matrix mix. Also, more than a 20% simethicone content may mean that some of the simethicone is not sufficiently protected after the mixture is comminuted. The simethicone may constitute as little as 1% of the total weight of its mixture with the matrix composition, but this will require that a proportionately larger amount of the mix be taken as a dose to supply the usual simethicone dose of 20 to 40 mg. Best results are obtained if the simethicone is 5 to 10% of its mixture with the matrix composition.

It has been stated above that the cooled, brittle mixture of simethicone and the glycerol-corn syrup solids matrix composition may be reduced to a granular, particulate form in a variety of ways. Still another manner of obtaining particles of small size involves its extrusion, while still molten, through orifices of about 1/64 inch in diameter to form continuous filaments of this small size. These filaments are then broken into short lengths of about 1/64 inch. As this procedure is known in the art, a general description of it will suffice. Broadly considered, the molten mixture of the simethicone and the matrix composition is forced by a pump, or by a piston, or by gas pressure through a horizontal plate having plurality of orifices through it.

These emerging filaments drop through a cooling zone so that filaments solidify before they can become entangled with each other. This cooling zone may be the atmosphere, but a preferred procedure is to let the emerging filaments drop into a liquid pool in which the matrix composition is not soluble. This will quickly harden the filaments, especially if the liquid pool is at about 50° C., but it may be even cooler to approach its freezing point. A preferred liquid is ethanol as it will also dissolve and remove any free simethicone liquid which has escaped from the matrix composition and is on the exterior of the filaments.

If the filaments have been extruded into the air and have been collected after they harden, they may be subdivided by the action of rollers, balls, impellers, grinders and similar comminuting apparatus. The final granular particles, including those obtained by comminuting the solidified masses, should be washed in ethanol to remove the simethicone that is released by the filament breaking operation. The simethicone is then recovered from the ethanol by distilling off the ethanol, preferably under vacuum.

If the filaments have been extruded into a liquid pool, they may be broken up in that pool by a submerged revolving impeller rotating at about 1,500 to 2,000 r.p.m. The impact of the impeller blades breaks the filaments into extremely small lengths, about 1/64 inch, and this can be regulated by continuing to drive the impeller after the extrusion has ceased. Of course, the air hardened filaments can be transferred to such a liquid pool in which an impeller is operating so that fragmentation of the filaments occurs. The broken filaments are removed from the slurry, dried and used as described herein.

When the antacid or (antacids) is combined with the above described particles of simethicone and its matrix composition, the antacid content should weigh from 15 to 25 times the weight of the simethicone. For instance, if a dose is to contain 20 mg. of simethicone, the antacid should weigh from 300 to 500 mg. and preferably about 400 mg. Preferably, the antacid content is made up of a mixture of the usual ones present in conventional antacid tablets.

These gastric antacids include aluminum hydroxide, magnesium carbonate, magnesium trisilicate, sodium bicarbonate, calcium caseinate, magnesium oxide, calcium carbonate, magnesium hydroxide, aluminum aminoacetate, calcium phosphate, bismuth subcarbonate, aluminum trisilicate, magnesium phosphate, aluminum phosphate, dihydroxy aluminum aminoacetate, and potassium phosphate.

Simethicone has been referred to in the above description of the invention, but other silicon containing compounds or complexes having the same physiological or therapeutic properties and which are mentioned in the literature, may be used in place of the simethicone. These equivalent compounds are represented by the general chemical formula:

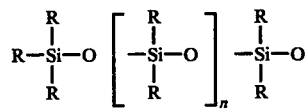

where R represents a lower alkyl group not exceeding 5 carbon atoms or an organic radical such as phenyl and n can be from 0 to 2000. Most advantageously, the siloxanes will be methylpolysiloxanes of at least 200 cs. viscosity at 25° C., preferably with a viscosity of between 250 and 1000 cs. at 25° C. Preferably the methylsiloxanes will contain from 1.9 to 2.1 methyl radicals per silicon atom.

As is stated above, the mixture of the antacid and the matrix protected simethicone may be put in hard shell capsules so that each one contains 10 to 20 mg. of the simethicone. One to four of them would be taken at a time to relieve flatulence. Or this mixture may be compressed into tablets with conventional tableting machines after having added to the mixture one or more of the usual excipients, binders, fillers, disintegrants or lubricants which are considered to be necessary. A preferred tablet will contain 20 mg. of simethicone, but it may be half to four times that amount.

The following examples are representative illustrations of the invention.

EXAMPLE 1

To 6 grams of glycerol is added 94 grams of corn syrup solids and it is heated to a temperature of about 120° C. while stirring or other agitation is carried on. After thorough blending is assured, 10 grams of simethicones are added and the agitation is continued. Heat may or may not be applied during this period if the temperature of the mixture remains above 90° C. On completion of this thorough blending, the molten mass is transferred to an extrusion apparatus, the orifice plate of which has a plurality of 1/64 inch diameter holes therethrough. It probably will be necessary to heat this extrusion apparatus to make sure that the filaments are continuously formed.

The filaments should drop into an ethanol pool at a temperature of about 50° C. so that they will rapidly harden. A submerged impeller within the ethanol pool is continuously rotated to break up the filaments by subjecting them to constant impact by the blades. An inspection will show when practically all of the filaments have been broken up to 1/64 inch lengths. The impeller is stopped and the slurry is allowed to stand for a day to assure dissolution of the extraneous simethicone. The slurry particles are then removed from the ethanol and dried.

The particles of simethicone entrapped within the matrix composition are then combined with 2 kg. of the selected antacid or antacid mixture, such as 1 kg. of aluminum hydroxide and 1 kg. of magnesium hydroxide. This final mixture is subdivided and put in capsules so that each one contains 20 mg. of simethicone. Or, if tableting excipients are added, the mixture is compressed into tablets so that each contains 20 mg. of the simethicone.

EXAMPLE 2

In Example 1, instead of the specified amounts of glycerol and corn syrup solids, there can be substituted two grams of glycerol and 98 grams of corn syrup solids. Ratios within these upper and lower limits may be utilized.

EXAMPLE 3

In Example 1, or the variations of Example 2, the amount of simethicone can be reduced to about 1 gram or be increased in amount up to about 20 grams.

EXAMPLE 4

To any of the matrix particles of the above Examples may be added from as little as 1.5 kg. of the antacid up to 2.5 kg.

EXAMPLE 5

The process of Example 1 is carried out up to the transfer of the molten mass to the extrusion step but, instead, it is poured in pans to a depth of a quarter to one-half inch, more or less. After it has cooled or been cooled to a brittle condition, it is comminuted to particles within a 12 to 14 guage size, using any of the processes mentioned above. These particles are washed in ethanol to remove any free simethicone and they may be used in this form or by combined with an antacid as described. The variations of the molten mass content described in Examples 2, 3 and 4 may be incorporated in this Example 5.

In the following claims, the word "simethicone" is intended to include not only simethicone per se, but in addition, under the doctrine of equivalent, a compound falling within the scope of the structural formual which is set forth and described in the specification above.

I claim:

1. A medicinal preparation for oral consumption to relieve flatulence which comprises simethicone entrapped in a matrix composition of glycerol and corn syrup solids, said glycerol amounting to from 2 to 15% of the weight of its mixture with the corn syrup solids and the simethicone amounting to from 1 to 20% of the weight of its mixture with the glycerol and the corn syrup solids.

2. The medicinal preparation of claim 1 in which the glycerol amounts to from 4 to 9% of the weight of its mixture with the corn syrup solids.

3. The medicinal preparation of claim 1 in which the simethicone amounts to from 5 to 10% of the weight of its mixture with the glycerol and corn syrup solids.

4. A medicinal preparation for oral consumption to relieve flatulence and hyperacidity which comprises a therapeutic antacid and simethicone, the simethicone being entrapped in a matrix composition of glycerol and corn syrup solids, said glycerol amounting to from 2 to 15% of the weight of its mixture with the corn syrup solids, the simethicone amounting to from 1 to 20% of the weight of its mixture with the glycerol and corn syrup solids and the antacid amounting to from 15 to 25 times the weight of the simethicone and matrix composition.

5. The medicinal preparation of claim 4 in which the antacid amounts to 20 times the weight of the simethicone and the matrix composition.

6. The medicinal preparation of claim 4 in which the glycerol amounts to from 4 to 9% of the weight of its mixture with the corn syrup solids, the simethicone amounts to from 5 to 10% of the weight of its mixture with the glycerol and corn syrup solids.

7. The process for making a medicinal preparation for oral consumption to relieve flatulence which comprises mixing together and heating to a molten state a matrix composition of glycerol and corn syrup solids, the glycerol amounting to from 2 to 15% of the weight of the mixture with the corn syrup solids, blending simethicone into said molten composition so that the simethicone amounts to from 1 to 20% of the weight of its mixture with the matrix composition, and producing from said molten blend solid discrete particles in which the simethicone is entrapped in the solid matrix particles.

8. The process of claim 7 in which said molten blend is extruded in filaments, the filaments are cooled and solidified and the solidified filaments are then ruptured into discrete particles.

9. The process of claim 7 in which said molten blend is poured to form a sheet which is then cooled to a brittle condition and the brittle mass is comminuted into discrete particles.

10. The process for making a medicinal preparation for oral consumption to relieve flatulence and hyperacidity which comprises mixing together and heating to a molten state a matrix composition of glycerol and corn syrup solids, the glycerol amounting to from 2 to 15% of the weight of the mixture with the corn syrup solids, blending simethicone into said molten composition so that the simethicone amounts to from 1 to 20% of the weight of its mixture with the matrix composition, and producing from said molten blend solid discrete particles in which the simethicone is entrapped in the solid matrix particles, and intimately combining a therapeutic antacid with said discrete particles in a quantity so that it amounts to from 15 to 25 times the weight of the simethicone and matrix composition.

11. The process of claim 10 in which at least two therapeutic antacid agents are intimately combined with said discrete particles.

12. The method of reducing stomach and intestinal gas in persons suffering from flatulence which involves orally administering to them a composition which comprises an effective amount of simethicone entrapped in discrete, comminuted particles of a matrix of glycerol and corn syrup solids, the glycerol amounting to from 2 to 15% of the weight of said matrix and the simethicone amounting to from 1 to 20% of the weight of its mixture with the matrix.

13. The method of claim 12 in which said amount is at least 20 mg. of simethicone.

14. The method of claim 12 which includes the concomitant administration to the persons, by inclusion in said composition, of an antacid to reduce hyperacidic conditions, said antacid weighing from 15 to 25 times the simethicone weight.

* * * * *